US00PP08092P

United States Patent [19]

Austin

[11] Patent Number: Plant 8,092

[45] Date of Patent: Jan. 12, 1993

[54] ROSE PLANT—'AUSDIMINDO'

[75] Inventor: David C. H. Austin, Albrighton, England

[73] Assignee: David Austin Roses, Albrighton, England

[21] Appl. No.: 623,304

[22] Filed: Dec. 6, 1990

[51] Int. Cl.[5] ..... A01H 5/00

[52] U.S. Cl. ..... Plt./1

[58] Field of Search ..... Plt. 1, 22, 26

*Primary Examiner*—Howard J. Locker

*Attorney, Agent, or Firm*—Ladas & Parry

[57] ABSTRACT

A new variety of rose plant of the shrubb class distinctive in its character by its fully double, pure pink flowers with abundant continual blooming, and the unusual shaping of the flowers.

1 Drawing Sheet

BACKGROUND OF THE INVENTION

The present invention relates to a new and distinct variety of shrub roses, said new variety originating as a single seedling resulting from a definite effort to produce an improvement in this class of rose.

BRIEF SUMMARY OF THE INVENTION

Primary features of this new variety which connote a distinctive advance over existing types are the vigorous abundant and continual blooming that occurs for 5 months taken with the perfection of the fully double flowers of an old-fashioned shape, more particularly apparent in the accompanying illustration of a specimen thereof.

The accompanying illustration shows typical cultivar flowers of this new cultivar in various stages of development, depicted in color as nearly true as is possible to make the same in color illustrations of this character.

DETAILED BOTANICAL DESCRIPTION

The following is a detailed description of the new variety, color terminology being in accordance with the "Methuen Handbook of Colour" published by Eyre Methuen Ltd (1963).

Variety denomination (in accordance with the UPOV Convention):

Ausdimindo (Cultivar Trade Name: Bibi Maizoon).

Type: Hardy, outdoor, bushy, garden decoration.

Class: Shrub.

Propagation: This variety holds its distinguishing characteristics through succeeding propagations by budding.

Asexual reproduction of the new cultivar by budding has taken place at a nursery in Albrighton, Nr. Wolverhampton, England and was derived as follows:

Female parent (seed parent): The Reeve (non-patented).

Male parent (pollen parent): Chaucer (non-patented).

The operation of the artificial pollination is therefore expressed by the following: The Reeve×Chaucer.

The following observations are made of specimens grown outdoors in England.

PLANT DESCRIPTION

Plant:

*Height.*—90 cm.

*Habit.*—Low and mounted growth.

Branches:

*Young stems.*—Color: 29C7 Apple green with extensive violet brown tint 10F6. Texture: Smooth. Thorns: Sparse glandular hairs 3–8 thorns per node hairs & thorns brownish red 10D7 (raspberry).

*Old stems.*—Color: 29D6 Greyish green with extensive purplish red 11D7 tint. Texture: Smooth and glabrous. Thorns: 2–8 per node, 1.7 mm long, 10D8 brownish red (strawberry).

Leaves:

*Stipules.*—Length: Av. 25 mm. Width: Av. 8 mm (Max). Angle of wingtips to petiole: Less than 45°. Color: 2B4. Margins: With red glandular hairs. Shape: Rounded (convex).

Petiole:

*General description.*—Slender.

*Length.*—Av. 65 mm.

*Upperside color.*—29C7 Greyish green.

*Groove/hairs/thorns.*—Sparse red glandular hairs.

*Underside.*—30D4 Light green.

*Hair/thorns.*—1–3 per node, Brownish red 8E8 fading to pale yellow.

*Leaflets.*—Number: 5, 7. Shape: Ovate with rounded base and cuspidate apex. Serration: Dentate. Texture: Leathery.

General effect of foliage: Rather sparse.

*Color.*—Young foliage. Upperside: 3E7 Olive with reddish brown 9E7 capillaries and margins. Underside: 9E5 Reddish brown. Adult foliage. Upperside: 29F7 Dark green. Underside: 29E6 Spinach green.

Inflorescence

Number of flowers per stem: 1 to 6 (mainly 5).

Peduncle:

*Length.*—About 40 mm.

*Color.*—Sparse red glandular hairs, 1C6 greyish. green widely shaded with reddish brown 8D5/6.

*Thorns/hairs.*—Small thorns.

Sepals:

*Upperside color.*—29D7/8 Greyish green/Deep green.

*Outer margins.*—With red glandular hairs and long ensiform protrusions (margins of protrusions dentate).

*Inner margins.*—Densely tomentose.

*Underside color.*—Ensiform protrusions shaded with reddish brown 8D5.

Outside and Inside texture: Densely tomentose.

*Sepal length.*—25–35 mm.

*Bud shape.*—Rounded with cuspidate apex.

*Length.*—About 35 mm.

*Max. width.*—10 mm before bud break.

*Color when opening.*—30A3 Pale green at base deepening through cream greyish rose 11B6 and deep red 11C8.

*Flower shape.*—As a flattened cup.

*Diameter.*—About 70 mm.

Flower color when opening:

*Upperside.*—Outer petals: 12A3 pale red (yellow at base). Inner petals: 11A5.

*Underside.*—Outer petals: 11A2 Pinkish white (pale yellow at base. Inner petals: 11A4.

Flower color when blooming:

| | Outer Petals | Inner Petals |
|---|---|---|
| Upperside | 12A2 Pinkish white. | 11A3 Pale red. |
| Underside | 13A2 Pinkish white. | 11A3 Pale red. |

Flower coloring when finished blooming:

*Upperside.*—Outer petals: 12A2 Pinkish white. Inner petals: 11A4.

*Underside.*—Outer petals: 12A2 Pale pinkish white. Inner petals: 11A3.

Length of blooming season at production location: From June to October.

Fragrance: Very sweet.

Lasting quality: Good. Range in number of days on plant is 6–8 days. Range in number of days as cut flowers is 5–7 days.

Petals:

*Shape.*—Outside: Rounded with flattened bilobed apex cuneate base. Middle: Ovate with flattened and bilobed apex cuneate base. Inside: Similar to middle but narrower. Texture: Irregular/grainy. Number: 110–120 inner and 10 slightly exhibiting staminody. Cleaning: Good, the petals fall easily and leave a tidy rose.

Stamens:

*Number.*—32–38 (average 35).

*Anthers.*—Bright yellow 3A6.

*Filaments.*—Irregular heights pale yellow 3A4.

Pistils:

*Numbers.*—50–60.

*Stigmas.*—Yellow 3A3.

*Styles.*—Irregular heights pale straw color 3A2.

Receptacle:

*Color.*—29D7 Greyish green.

*Texture.*—Smooth glabrous.

*Size.*—Length 10–12 mm. Max. width 8 mm or 9 mm.

*Shape.*—Jug shaped.

The development:

*Vegetation.*—Moderately vigorous.

*Blooming.*—Continual.

*Aptitude to bearing fruits.*—None.

*Resistance to frost.*—Good.

*Resistance to disease.*—Good.

I claim:

1. A new and distinct variety of rose plant of the shrub class, characterized as to novelty by its fully double flowers of pure pink coloring, with abundant and continual blooming and the unusual blend of coloring and shaping of the flower being substantially as shown and described.

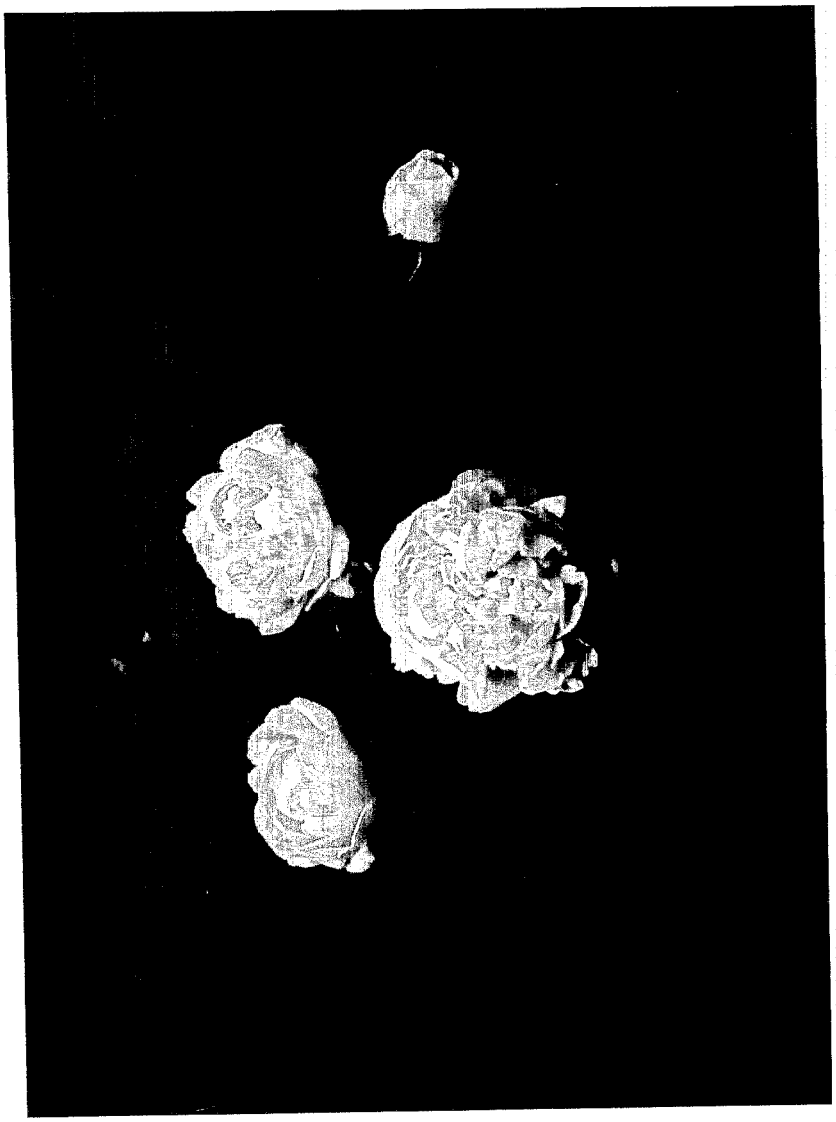

* * * * *